US011191881B2

(12) United States Patent
Quiroz et al.

(10) Patent No.: US 11,191,881 B2
(45) Date of Patent: Dec. 7, 2021

(54) ARTICLES FOR WARMING AND MONITORING PATIENT DURING DIALYSIS TREATMENT

(71) Applicant: Fresenius Medical Care Holdings, Inc., Waltham, MA (US)

(72) Inventors: Erik A. Quiroz, Benicia, CA (US); Jon Moss, Antioch, CA (US); Bert D. Egley, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 777 days.

(21) Appl. No.: 15/841,020

(22) Filed: Dec. 13, 2017

(65) Prior Publication Data

US 2019/0175810 A1 Jun. 13, 2019

(51) Int. Cl.
*A61M 1/16* (2006.01)
*A61M 1/28* (2006.01)
(Continued)

(52) U.S. Cl.
CPC ......... *A61M 1/1601* (2014.02); *A61B 5/0002* (2013.01); *A61B 5/022* (2013.01);
(Continued)

(58) Field of Classification Search
CPC ........ A61M 1/1601; A61M 1/28; A61M 1/14; A61F 7/007; A61F 7/0097; A61B 5/4836; A61B 5/02055; A61B 5/02438; A61B 5/0002; A61B 5/02042; A61B 5/022; A61B 5/6866
See application file for complete search history.

(56) References Cited

U.S. PATENT DOCUMENTS 5,160,828 A 11/1992 Olsen
5,785,716 A 7/1998 Bayron et al.
(Continued)

FOREIGN PATENT DOCUMENTS

CN 204132479 2/2015
DE 102005019868 11/2006
(Continued)

OTHER PUBLICATIONS

International Search Report and Written Opinion in Application No. PCT/US2018/064417, dated Mar. 11, 2019, 13 pages.
(Continued)

*Primary Examiner* — Philip R Wiest
(74) *Attorney, Agent, or Firm* — Fish & Richardson P.C.

(57) ABSTRACT

An article configured to warm and monitor a patient during a dialysis treatment, the article includes one or more heating elements. The article also includes one or more sensors configured to monitor a condition of the patient during the dialysis treatment. The article also includes a fabric portion configured to receive the one or more heating elements and the one or more sensors and position the one or more heating elements and the one or more sensors on the patient during treatment. The article also includes a transmitter configured to transmit information from the one or more sensors to a dialysis machine and an electrical connector configured to provide power to at least one of the one or more heating elements and the one or more sensors.

28 Claims, 4 Drawing Sheets

(51) Int. Cl.

| | | |
|---|---|---|
| *A61M 1/36* | (2006.01) | |
| *A61B 5/00* | (2006.01) | |
| *A61F 7/00* | (2006.01) | |
| *A61B 5/0205* | (2006.01) | |
| *A61B 5/024* | (2006.01) | |
| *A61B 5/02* | (2006.01) | |
| *A61M 1/14* | (2006.01) | |
| *A61B 5/022* | (2006.01) | |
| *A61B 5/1455* | (2006.01) | |
| *A61F 7/02* | (2006.01) | |

(52) U.S. Cl.
CPC ...... *A61B 5/02042* (2013.01); *A61B 5/02055* (2013.01); *A61B 5/02438* (2013.01); *A61B 5/4836* (2013.01); *A61B 5/6806* (2013.01); *A61B 5/6807* (2013.01); *A61B 5/6866* (2013.01); *A61F 7/007* (2013.01); *A61F 7/0097* (2013.01); *A61M 1/14* (2013.01); *A61M 1/28* (2013.01); *A61M 1/282* (2014.02); *A61M 1/3656* (2014.02); *A61B 5/14552* (2013.01); *A61F 2007/0036* (2013.01); *A61F 2007/0045* (2013.01); *A61F 2007/0096* (2013.01); *A61F 2007/0233* (2013.01); *A61M 2205/15* (2013.01); *A61M 2205/18* (2013.01); *A61M 2205/3368* (2013.01); *A61M 2205/3576* (2013.01); *A61M 2205/36* (2013.01); *A61M 2205/3653* (2013.01); *A61M 2230/00* (2013.01); *A61M 2230/06* (2013.01); *A61M 2230/30* (2013.01); *A61M 2230/50* (2013.01)

(56) References Cited

U.S. PATENT DOCUMENTS

| | | | |
|---|---|---|---|
| 6,248,064 B1 * | 6/2001 | Gopinathan | A61B 5/0006 600/300 |
| 6,582,456 B1 | 6/2003 | Hand et al. | |
| 6,840,955 B2 | 1/2005 | Ein | |
| 2002/0019654 A1 | 2/2002 | Ellis et al. | |
| 2002/0026226 A1 * | 2/2002 | Ein | A61F 7/007 607/108 |
| 2002/0143259 A1 * | 10/2002 | Stergiopoulos | A61B 5/025 600/490 |
| 2005/0034485 A1 | 2/2005 | Klefstad-Sillonville et al. | |
| 2007/0049997 A1 | 3/2007 | Fields et al. | |
| 2007/0078324 A1 | 4/2007 | Wijisiriwardana | |
| 2008/0033518 A1 | 2/2008 | Rousso et al. | |
| 2011/0066043 A1 * | 3/2011 | Banet | A61B 5/022 600/485 |
| 2013/0225966 A1 | 8/2013 | Macia Barber et al. | |
| 2014/0183106 A1 * | 7/2014 | Kotsos | A61M 1/1601 210/85 |
| 2014/0343390 A1 | 11/2014 | Berzowska et al. | |
| 2016/0081846 A1 | 3/2016 | Katzenstein | |
| 2016/0262924 A1 * | 9/2016 | Abreu | A41D 19/0027 |
| 2017/0106151 A1 | 4/2017 | Schmidt et al. | |

FOREIGN PATENT DOCUMENTS

| | | |
|---|---|---|
| DE | 202006019535 | 5/2007 |
| JP | H08141075 | 6/1996 |
| WO | WO 2004/093758 | 11/2004 |
| WO | WO 2017/035341 | 3/2017 |

OTHER PUBLICATIONS

PCT International Preliminary Report on Patentability in Application No. PCT/EP2018/064417, dated Jun. 16, 2020, 8 pages.

* cited by examiner

ARTICLES FOR WARMING AND MONITORING PATIENT DURING DIALYSIS TREATMENT

TECHNICAL FIELD

This disclosure relates to articles for warming and monitoring a patient during a dialysis treatment.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

SUMMARY

In one aspect, an article configured to warm and monitor a patient during a dialysis treatment, the article includes one or more heating elements. The article also includes one or more sensors configured to monitor a condition of the patient during the dialysis treatment. The article also includes a fabric portion configured to receive the one or more heating elements and the one or more sensors and position the one or more heating elements and the one or more sensors on the patient during treatment. The article also includes a transmitter configured to transmit information from the one or more sensors to a dialysis machine and an electrical connector configured to provide power to at least one of the one or more heating elements and the one or more sensors.

In some implementations, the one or more heating elements are individually controllable.

In some implementations, the one or more sensors includes an ambient temperature sensor configured to monitor an ambient temperature of a space in which the dialysis treatment is occurring.

In some implementations, the one or more sensors includes a blood oxygen monitor. In some implementations, the one or more sensors includes a blood pressure monitor. In some implementations, the one or more sensors includes a heart rate monitor. In some implementations, the one or more sensors includes a temperature sensor.

In some implementations, the one or more sensors includes a wetness sensor. In some cases, the wetness sensor is configured to be positioned proximate to a patient access and is configured to detect a leak at the patient access when the article is on the patient.

In some implementations, the one or more sensors includes an accelerometer.

In some implementations, the article is a glove. In some implementations, wherein the article is a sock. In some implementations, the article is a blanket or a wrap.

In some implementations, the one or more heating elements are separable from the fabric portion of the article. In some implementations, the one or more sensors are separable from the fabric portion of the article.

In another aspect, a dialysis system includes a dialysis machine and an article configured to communicate with the dialysis machine during a dialysis treatment. The article includes one or more heating elements. The article also includes one or more sensors configured to monitor a condition of the patient during the dialysis treatment. The article also includes a fabric portion configured to receive the one or more heating elements and the one or more sensors and position the one or more heating elements and the one or more sensors on the patient during treatment. The article also includes a transmitter configured to transmit information from the one or more sensors to the dialysis machine and an electrical connector configured to provide power to at least one of the one or more heating elements and the one or more sensors.

In some implementations, the electrical connector connects the article to the hemodialysis machine.

In some implementations, the dialysis machine includes a controller configured to determine a condition of a patient based on the information transmitted to the dialysis machine from the transmitter. In some cases, the controller is further configured to raise an alarm on the dialysis machine based on a determined condition of the patient. In some cases, the condition of the patient comprises information that the patient is disconnected from the dialysis machine.

In another aspect, a method of heating and monitoring a patient during a dialysis treatment using an article positioned on the patient includes heating, by one or more heating elements of the article, an area of the patient. The method also includes monitoring, using one or more sensors of the article, a condition of the patient. The method also includes transmitting, from a transmitter of the article to a dialysis machine, information from the one or more sensors.

In some implementations, the one or more heating elements are individually controllable.

In some implementations, the article is a glove, a sock, a blanket, or a wrap.

Advantages of the foregoing may include, but are not limited to, one or more of those described below and herein elsewhere.

In some implementations, the article includes heating elements to provide heating to the patient at areas on their body, for example their extremities, where they may feel cold during a dialysis treatment. In some instances, the amount of heating and the location of heating may be adjustable during treatment based on patient comfort.

In some implementations, the article includes one or more sensors to monitor patient vital signs or other parameters (e.g. blood pressure, heart rate, body temperature, etc.) during dialysis treatment. Because the article fits to the patient's anatomy, the article holds the sensors more securely to the patient which may reduce the likelihood of errors by the sensors caused by movement or disconnection.

In some implementations, the sensors and/or heating elements are removable from the article and can be cleaned. As such, the sensors and/or heating elements can be used in treating multiple patients and can be cleaned between patients. As a result, using the article to heat and monitor patients is cost efficient and sanitary.

In some implementations, the sensors in the article can detect patient conditions and the article can provide patient bio-feedback to the dialysis machine. The bio-feedback received at the dialysis machine allows the dialysis machine to raise alarms (e.g. a possible disconnect alarm) and/or adjust treatment parameters based on the bio-feedback. As a result, more efficient dialysis treatment can be performed.

The details of one or more implementations are set forth in the accompanying drawings and the description below. Other aspects and advantages will be apparent from the description and drawings, and from the claims.

DETAILED DESCRIPTION

During a hemodialysis treatment, a patient's blood is circulated outside of the patient's body to be cleaned of toxins. During a peritoneal dialysis treatment, fluid is exchanged with the patient in a peritoneal cavity to remove toxins from the patient. In some cases, both of these procedures may cool the body temperature of the patient to where the patient, or certain body parts of the patient, feel uncomfortably cold.

In one aspect, a warming and monitoring garment can be placed on the patient to warm the patient using one or more heating elements and to monitor attributes of the patient during treatment to be sent to the dialysis machine. The garment may, for example, monitor the patient's body temperature, blood pressure, heart rate, and/or blood oxygen level during treatment. The garment may also monitor a status of the patient access, e.g., by using a wetness detector to detect leaking at the access or by using an accelerometer which may detect patient movement near the access. The garment may communicate with the dialysis machine to provide patient data gathered by the monitoring devices. The dialysis machine may process the data and raise alarms, provide instructions (e.g. heating instructions) to the garment, and/or display the data.

Overview of System

Figure 1:
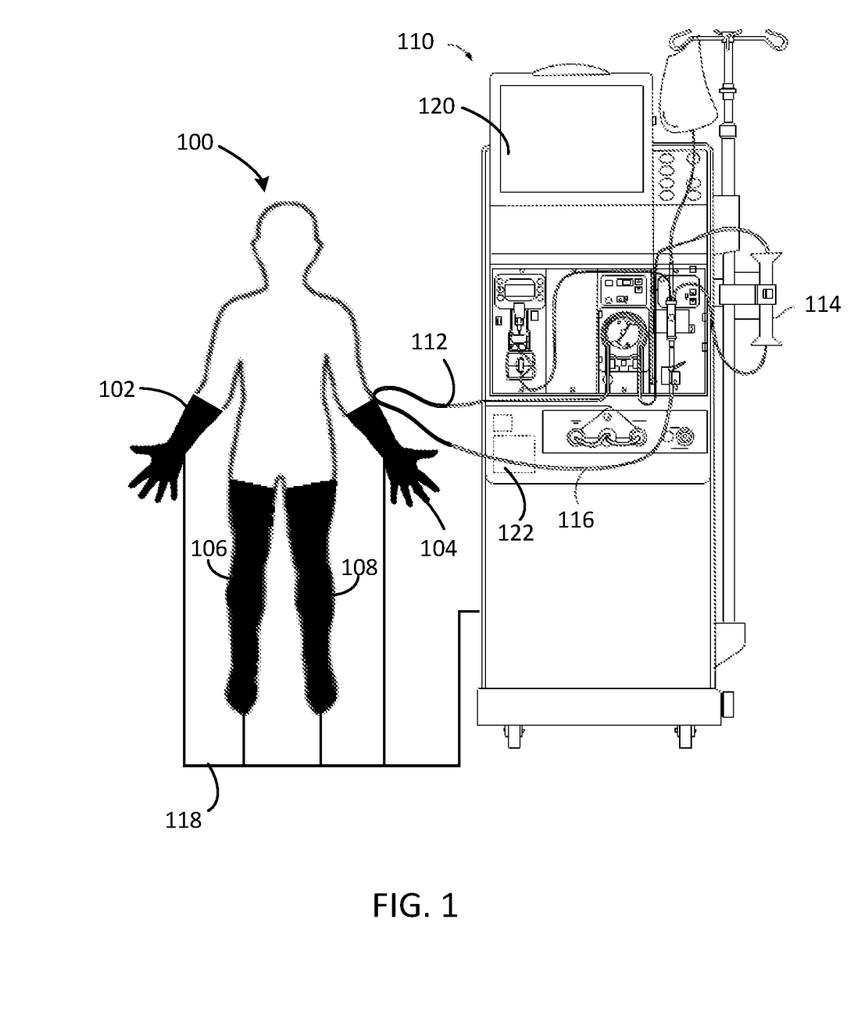
FIG. 1 illustrates a patient undergoing hemodialysis treatment wearing warming and monitoring gloves and socks connected to a hemodialysis machine.

FIG. 1 is a schematic of a patient 100 undergoing a hemodialysis treatment and wearing warming and monitoring gloves 102 and 104, and warming and monitoring socks 106 and 108. The patient 100, the gloves 102 and 104, and the socks 106 and 108, are connected to a hemodialysis machine 110. The patient 100 is connected to an arterial line 112 of the hemodialysis machine 110 by a needle access on the patient's forearm. During treatment, the patient's blood flows through the needle access and into the arterial line 112. The arterial line 112 delivers the blood to a dialyzer 114 of the hemodialysis machine 110. In the dialyzer 114, a semipermeable membrane separates the blood from a dialysate fluid. The dialyzer 114 cleans the blood as toxins flow from the blood, through the semipermeable membrane, and into the dialysis fluid. The cleaned blood flows out of the dialyzer 114 and into a venous line 116. The venous line 116 is connected to the patient at a second needle access on the patient's forearm. During treatment, the cleaned blood flows from the venous line 116, through the second needle access, and back into the patient.

During the hemodialysis treatment, as the patient's blood circulates through arterial and venous lines 112 and 116 and through the dialyzer 114, the blood loses temperature. As such, the blood returned to the patient 100 by the venous line 116 is cooler than the blood removed from the patient 100 by the arterial line 112. This drop in blood temperature may cause the patient to feel cold, especially at their extremities, e.g. their hands and their feet.

The gloves 102 and 104 and the socks 106 and 108 include heating elements that are configured to warm the patient 100 during a hemodialysis treatment. The gloves 102 and 104 and the socks 106 and 108 are connected to and receive power from the hemodialysis machine 110 via wires 118. One or more sensors are also included in the gloves 102 and 104 and the socks 106 and 108 that detect conditions of the patient 100 during hemodialysis treatment.

Warming and Monitoring Articles

Figure 2A:
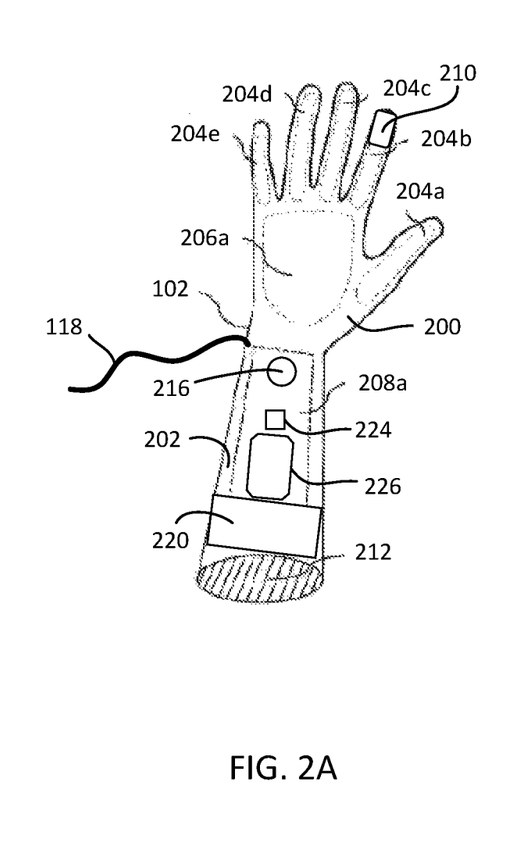
FIG. 2A is a schematic of a front side of one of the warming and monitoring gloves as worn by the patient in FIG. 1.
Figure 2B:
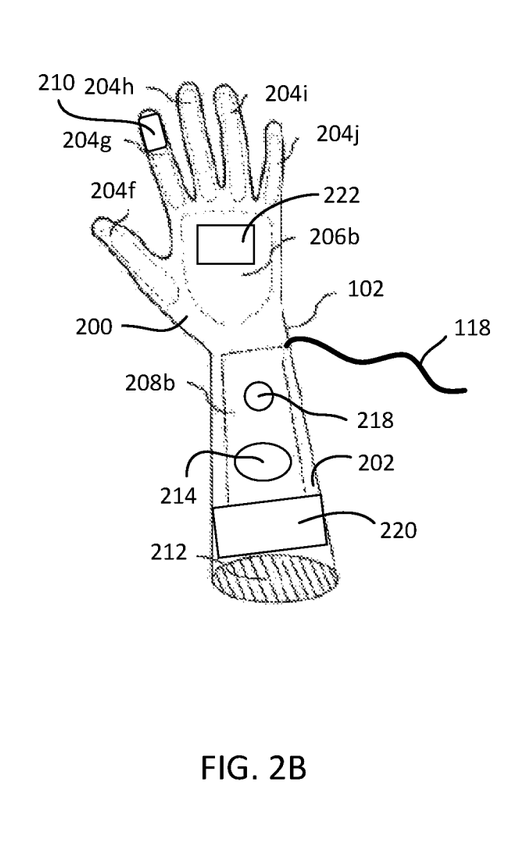
FIG. 2B is a schematic of a back side of one of the warming and monitoring gloves as worn by the patient in FIG. 1.

FIGS. 2A and 2B are illustrations of a front side (FIG. 2A) and a back side (FIG. 2B) of the glove 102 worn by the patient 100 in FIG. 1. The glove 102 includes a hand-covering portion 200 and a forearm sleeve 202. The hand-covering portion 200 and the forearm sleeve 202 are made of a flexible fabric (e.g., wool, cotton, linen, silk, nylon, polyester, spandex, and rayon) that provides insulation to the patient's hand and forearm. The hand-covering portion 200 includes finger heating elements 204a-204e and a palm heating element 206a on the front side of the glove 102 shown in FIG. 2A. The front side of the glove 102 also includes a forearm heating element 208a.

As shown in FIG. 2B, the back side of the glove 102 includes finger heating elements 204f-j and a back-of-hand heating element 206b. The back side of the glove 102 also includes a second forearm heating element 208b. The heating elements 204a-j, 206a-b, and 208a-b are removable from the glove 102. The heating elements 204a-j, 206a-b, and 208a-b fit into pockets in the glove 102 or are attached to specific places on the glove 102 with hook and loop fasteners, depending on the required heating element positioning on the patient 100. The heating elements 204a-j, 206a-b, and 208a-b, are individually controllable, i.e., can be turned off and on independently of one another by a control device 222. The control device 222 has a touch screen allowing for individual heating elements to be selected. The heating elements 204a-j, 206a-b, and 208a-b are dispersed in a pattern across the glove 102 to cover multiple areas of the hand and arm. The glove 102 includes a wire 118 to connect the glove 102 to the hemodialysis machine 110. The heating elements 204a-j, 206a-b, and 208a-b receive power through the wire 118.

The glove 102 also includes sensors which are removable from the glove 102. The sensors fit into pockets or are attached to specific places on the glove with hook and loop fasteners, depending on the required sensor positioning on the patient. In FIG. 2A, a wetness sensor 226, as it contacts the patient's skin, is attached with hook and loop fasteners to the glove 102, rather than slid inside a pocket. The glove 102 allows the sensors to be securely held in place during treatment, which may reduce the frequency of errors in sensor data caused by a sensor being out of place or disconnected from the patient 100. As the sensors and the heating elements are removable, the sensors and the heating elements may be removed from the glove and cleaned between treatments.

The sensors send sensor data to a transmitter 214 via wired connections with the transmitter 214. The transmitter 214 then transmits the sensor data wirelessly (e.g. via Bluetooth or Wi-Fi) to the hemodialysis machine 110. The sensor data is used by the hemodialysis machine 110 to monitor the patient 100, to adjust parameters of the hemodialysis treatment, and/or to raise alarms during treatment.

The glove 102 includes two temperature sensors 216 and 218. The first temperature sensor 216 is located on the front of the glove 102 and measures a body temperature of the patient 100. The second temperature sensor 218 is located on the back of the glove 102 and measures an ambient temperature of the environment in which the hemodialysis treatment is taking place. The patient's body temperature and the ambient temperature are sent to the transmitter 214 for transmission to the hemodialysis machine 110.

The glove 102 also includes a blood pressure cuff 220 in the forearm sleeve 202 of the glove 102. The blood pressure cuff 220 inflates and deflates automatically to take the patient's blood pressure at set intervals. The blood pressure cuff 220 sends the blood pressure data to the transmitter 214 for transmission to the hemodialysis machine 110.

The glove 102 also includes a blood oxygen sensor 210 in one of the fingers of the glove 102. Here, the blood oxygen sensor 210 is a pulse oximeter which is configured to determine the blood oxygen level of the patient 100 as well as the patient's pulse, thereby also functioning as a heart rate sensor. The blood oxygen sensor 210 clamps on the top and bottom of the patient's index finger and determines the patient's pulse and blood oxygen level. The blood oxygen sensor 210 sends the pulse and blood oxygen data to the transmitter 214 for transmission to the hemodialysis machine 110.

On the front side of the forearm sleeve 202, as shown in FIG. 2A, the glove 102 includes an accelerometer 224 and a wetness sensor 226. The accelerometer 224 and the wetness sensor 226 are placed on the front side of the forearm sleeve 202 such that they are proximate to a location of the patient's vascular access on the patient's forearm. The wetness sensor 226 is positioned in the glove such that the wetness sensor 226 may detect moisture leaking out from the patient's vascular access. The accelerometer 224 senses acceleration of the patient's arm. The wetness sensor 226 sends data to the transmitter 214 for transmission to the hemodialysis machine 110. The accelerometer 224 sends acceleration data to the transmitter 214 for transmission to the hemodialysis machine 110.

A controller 122 of the dialysis machine 110 can receive and transmit electrical signals to and from systems of the dialysis machine 110. For example, the controller 122 can receive electrical signals from the transmitter of the glove 102 shown in FIGS. 2A-2B. The electrical signals indicate a status of the patient 100 during dialysis treatment. Based on the electrical signals, the controller 122 can modify operations of components of the dialysis machine 110, such as a pump speed of the peristaltic pump, a display, and other electrical and electromechanical systems. The dialysis machine 110 can present information received from the transmitter 214 (e.g. body temperature, heart rate, blood oxygen level, etc.) on a display 120. For example, the dialysis machine 110 may also present alarms or messages to an operator or patient 100 on the display 120, including disconnection alarms and movement warnings. The dialysis machine 110 may also present warning information on the display 120, for example, a diagram of which heating pads are turned on in a glove 102 or a sock 106 being worn by the patient 100 during treatment may be graphically shown on the display 120.

During treatment, the controller 122 of the hemodialysis machine 110 can combine acceleration data from the accelerometer 224 with wetness data from the wetness sensor 226 and data from other sensors in the hemodialysis system, e.g., a venous pressure sensor and an arterial pressure sensor, to monitor the patient 100 and/or the treatment. Based on the acceleration data from the accelerometer 224 and the wetness data from the wetness sensor 226, and data from other sensors, the controller 122 of the hemodialysis machine 110 may calculate, for example, that any number of states (e.g. connection, leak, disconnection) have occurred at the patient's access.

The sensors in the glove 102 are wired to the transmitter 214 and communicate sensor data to the transmitter 214 via the wires. The transmitter 214 wirelessly communicates the sensor data to the hemodialysis machine 110 during treatment. The glove 102 also includes an electrical cable 118 that attaches to the dialysis machine 110 and provides power to the heating elements 204a-j, 206a-b, and 208a-b and sensors of the glove 102.

Figure 3A:
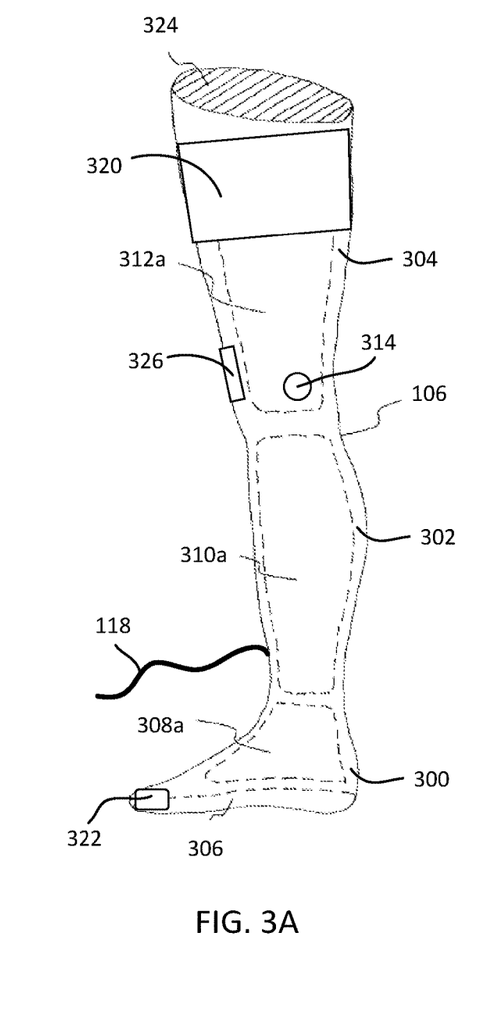
FIG. 3A is a schematic of an inside of one of the warming and monitoring socks as worn by the patient in FIG. 1.
Figure 3B:
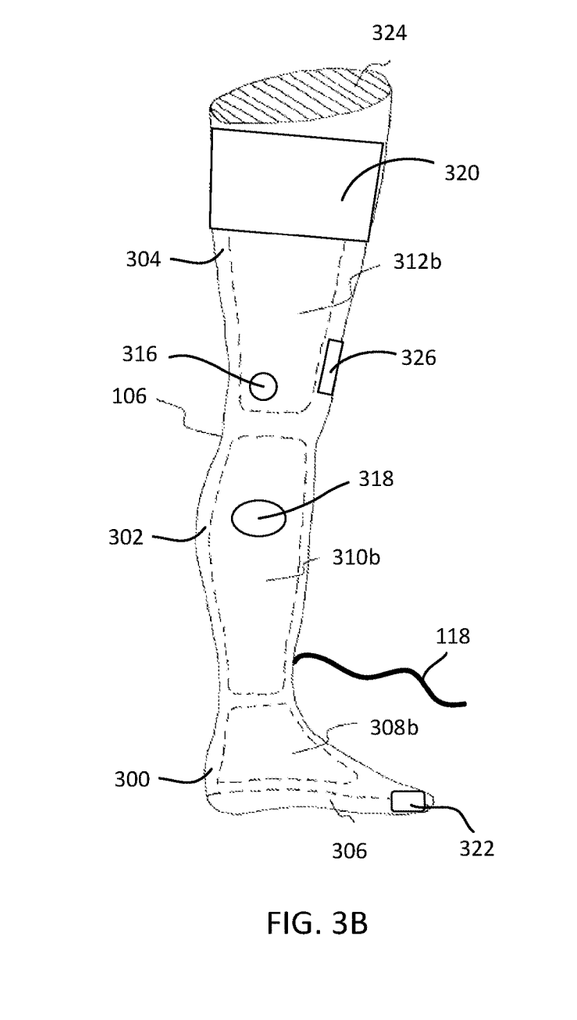
FIG. 3B is a schematic of an outside of one of the warming and monitoring socks as worn by the patient in FIG. 1.

FIGS. 3A and 3B are illustrations of an inside (FIG. 3A) and an outside (FIG. 3B) of the sock 106 worn by the patient 100 in FIG. 1. The sock 106 includes a foot portion 300, a lower leg portion 302, and an upper leg portion 304. The foot portion 300, the lower leg portion 302, and the upper leg portion 304 are made of a flexible fabric (e.g., wool, cotton, linen, silk, nylon, polyester, spandex, and rayon) that also provides insulation to the patient 100. The foot portion 300 includes a bottom heating element 306 and two ankle heating elements 308a-b. The lower leg portion 302 includes two lower leg heating elements 310a-b and the upper leg portion includes two upper leg heating elements 312a-b. The heating elements 306, 308a-b, and 310a-b are removable from the stock 106. The heating elements 306, 308a-b, and 310a-b fit into pockets in the sock 106 or are attached to specific places on the sock 106 with hook and loop fasteners, depending on the required heating element positioning on the patient 100. The heating elements 306, 308a-b, and 310a-b are individually controllable, i.e., can be turned off and on independently of one another by a control device 326. The control device 326 has a touch screen allowing for individual heating elements to be selected. The sock 106 includes a wire 314 to connect the sock 106 to the hemodialysis machine 110. The heating elements 306, 308a-b, and 310a-b receive power through the wire 314.

The sock 106 also includes sensors which are removable from the sock 106. The sensors fit into pockets in the sock 106 or are attached to specific places on the sock 106 with hook and loop fasteners, depending on the required sensor positioning on the patient 100. The sock 106 allows the sensors to be securely held in place during the dialysis treatment, which may reduce the frequency of errors in sensor data caused by a sensor being out of place or disconnected from the patient 100. As the sensors and the heating elements are removable, the sensors and the heating elements may be removed from the glove and cleaned between treatments.

The sensors send sensor data to a transmitter 318 via wired connections with the transmitter 318. The transmitter 318 then transmits the sensor data wirelessly (e.g. via Bluetooth or Wi-Fi) to the hemodialysis machine 110. The sensor data is used by the hemodialysis machine 110 to monitor the patient 100, to adjust parameters of the hemodialysis treatment, and/or to raise alarms during treatment.

The sock 106 includes two temperature sensors 314 and 316. The first temperature sensor 314 is located on the inside of the sock 106 and measures a body temperature of the patient 100. The second temperature sensor 316 is located on the back of the sock 106 and measures an ambient temperature of the environment in which the hemodialysis treatment is taking place. The patient's body temperature and the ambient temperature are sent to the transmitter 318 for transmission to the hemodialysis machine 110.

The sock 106 also includes a blood pressure cuff 320 in the upper leg portion 304 of the sock 106. The blood pressure cuff 320 inflates and deflates automatically to take the patient's blood pressure at set intervals. The blood pressure cuff 320 sends the blood pressure data to the transmitter 318 for transmission to the hemodialysis machine 110.

The sock 106 also includes a blood oxygen sensor 322 in one of the toes of the sock 106. Here, the blood oxygen sensor 322 is a pulse oximeter which is configured to determine the blood oxygen level of the patient 100 as well as the patient's pulse, thereby also functioning as a heart rate sensor. The blood oxygen sensor 322 clamps on the top and bottom of the patient's big toe and determines the patient's pulse and blood oxygen level. The blood oxygen sensor 322 sends the pulse and blood oxygen data to the transmitter 318 for transmission to the hemodialysis machine 110.

Methods of Use

A method of using an article (e.g. the warming and monitoring gloves 102 and 104, the warming and monitoring socks 106 and 108, or other warming and monitoring articles described herein) during a dialysis treatment of a patient is described herein.

An operator (e.g., a patient, a physician, a nurse, a medical practitioner) punctures an access site on skin of the patient to access a corporeal blood circuit of the patient. Before initiating the dialysis treatment, the operator disinfects and cleans skin of the patient and then inserts an arterial needle into an arterial access site and a venous needle into a venous access site. The arterial needle and the venous needle, when inserted, place the circulatory system of the patient 100 in fluid communication with the dialysis machine 110.

As shown in FIG. 1, after inserting the arterial needle and the venous needle, the operator places the gloves 102 and 104 and the socks 106 and 108 on the patient's hands and legs. To put on the glove 102, the patient 100 inserts his/her hand through the opening 212 and to put on the sock 106, the patient 100 inserts his/her leg through the opening 324. The sensors in the gloves 102 and 104 and the socks 106 and 108 are positioned on the patient 100 as the patient wears the gloves 102 and 104 and the socks 106 and 108. For example, the wetness sensor 226 is positioned over the skin of the patient 100 in the vicinity of the patient's access site when the patient is wearing glove 102. The flexible fabric of the glove 102 holds the wetness sensor 226 in the vicinity of the patient's access during treatment. The operator can shift the placement and/or orientation of the glove 102 such that the placement of the sensors is correct for the particular patient being treated.

The operator then initiates the dialysis treatment on the dialysis machine 110. Before initiating the dialysis treatment, the operator can set various dialysis treatment parameters of the dialysis machine 110. When the operator initiates the dialysis treatment, a peristaltic pump of the dialysis machine circulates the blood from the patient 100 through the dialyzer 114 to clean and filter the blood. Blood travels from the patient 100 through the arterial needle, along the arterial line set 112, and to the dialyzer 114. After the dialyzer 114 filters the blood, filtered blood exits the dialyzer 114 and travels along the venous line set 116 through the venous needle back to the patient 100. Within the dialyzer 114, alongside the flowing blood, a dialysis solution that can include salts, buffers, and/or acids removes toxins from the blood.

During treatment, the transmitters 214 and 318, in the glove 102 and the sock 106, respectively, receive information from their respective sensors and send that information to the hemodialysis machine 110. Transmitters in the glove 104 and the sock 108 also receive information from their respective sensors and send that information to the hemodialysis machine 110.

For example, when the wetness sensor 226 of the glove 104 during hemodialysis treatment sends data to the controller 122 of the hemodialysis machine 110 indicating that it is wet, the accelerometer 224 sends data to the hemodialysis machine 110 indicating that the arm containing the patient's access has moved at an acceleration rate that exceeds a predetermined threshold, and the venous pressure sensors send data to the hemodialysis machine indicating that the venous pressure is low, the hemodialysis machine 110 calculates that a venous disconnect has occurred and sounds an alarm. As another example, when the accelerometer 224 sends data to the hemodialysis machine 110 indicating that the arm containing the patient's access has moved at an acceleration rate that exceeds a predetermined threshold, but the data received from the wetness sensor 226 indicates that it is dry and the data received from the venous and arterial pressure sensors are pressures within the hemodialysis system's normal operating range, the hemodialysis machine calculates that the patient 100 has not been disconnected. In such a case, the hemodialysis machine sounds and displays an alarm warning the patient 100 to stop moving the arm containing his/her access.

Also, during treatment, the warming performed by the glove 102 and the sock 106 can be controlled by the patient. The patient 100 can control the heating elements in the gloves 102 and 104 and socks 106 and 108 using the control device 222. The control device allows individual heating elements, i.e., any one of heating elements 204a-j, 206a-b, and 208a-b, to be turned on or off independently of the others.

After the hemodialysis treatment is complete, the operator removes the gloves 102 and 104 and the socks 106 and 108 from the patient 100. The operator then disconnects the hemodialysis machine 110 from the patient by removing the arterial and venous needles from the patient's access. After the gloves 102 and 104 and the socks 106 and 108 are removed from the patient, the sensors and the heating elements may be removed from the gloves 102 and 104 and the socks 106 and 108. The sensors and the heating elements may be disinfected (e.g., by using a 1% bleach solution) before insertion into another pair of gloves or socks for a subsequent treatment. The flexible fabric portions of the gloves and socks may be washed before receiving sensors and heating elements for a subsequent treatment.

Alternative Implementations

The examples described herein can be implemented in a variety of ways without departing from the scope of the specification.

The warming and monitoring articles of FIGS. 1-3B have been described as being used in hemodialysis treatments. Though, in other implementations, the warming and monitoring articles can be used for other appropriate medical treatments. For example, the warming and monitoring articles described herein may be used during a peritoneal dialysis treatment. During peritoneal dialysis, dialysate is circulated through a catheter inside peritoneal cavity of a patient and absorbs waste products from blood vessels in the patient's peritoneum. The dialysate is then pumped out of the patient's body by a peritoneal dialysis machine. The patient may feel cold during a peritoneal dialysis procedure because the dialysate fluid may not be warmed all the way to body temperature and/or the exchange of waste products with the blood vessels in the peritoneum may cool the body temperature of the patient.

The warming and monitoring article may instead be a glove without a forearm sleeve, thereby covering only the patient's hand. The warming and monitoring article may instead be a sock, covering only the patient's lower leg and foot, or only the patient's foot. These alternative implementations of the warming and monitoring articles may not include all of the sensors and heating elements described above in relation to the glove 102 and the sock 106.

The heating elements in the glove 102 and the sock 106 have been described as separate heating elements that are individually controllable. In some implementations, there may be one heating element that wraps around a portion of the patient (e.g. a finger, the forearm, the lower leg) rather than separate heating elements on opposing sides of the article. In other implementations, there may be one large heating element in the article (e.g. a hand shaped heating element inside of a glove) that functions to heat an area of the patient. In some implementations, there may be a pattern of heating elements disposed in the article based on a location where the article is placed on a patient and the anatomy of that location. For example, heating elements may be disposed in a wrist portion of a glove where blood vessels are close to the surface of the skin. As such, heat may transfer more efficiently into the blood from the heating elements. In another example, there may be heating elements disposed in a portion of a wrap or blanket that can be positioned by a patients' underarm where blood vessels are also close to the surface.

While the warming and monitoring articles have been described as having removable heating elements and sensors, in some implementations, the heating elements and/or the sensors may be permanently attached to the article, rather than being removable. This may allow the heating elements and sensors to be sized based on patient anatomy and fit to a particular article. For example, gloves may be sized in small, medium, and large, and each would have differing sizes of heating elements based on the surface area of the skin needing to be heated.

Figure 4:
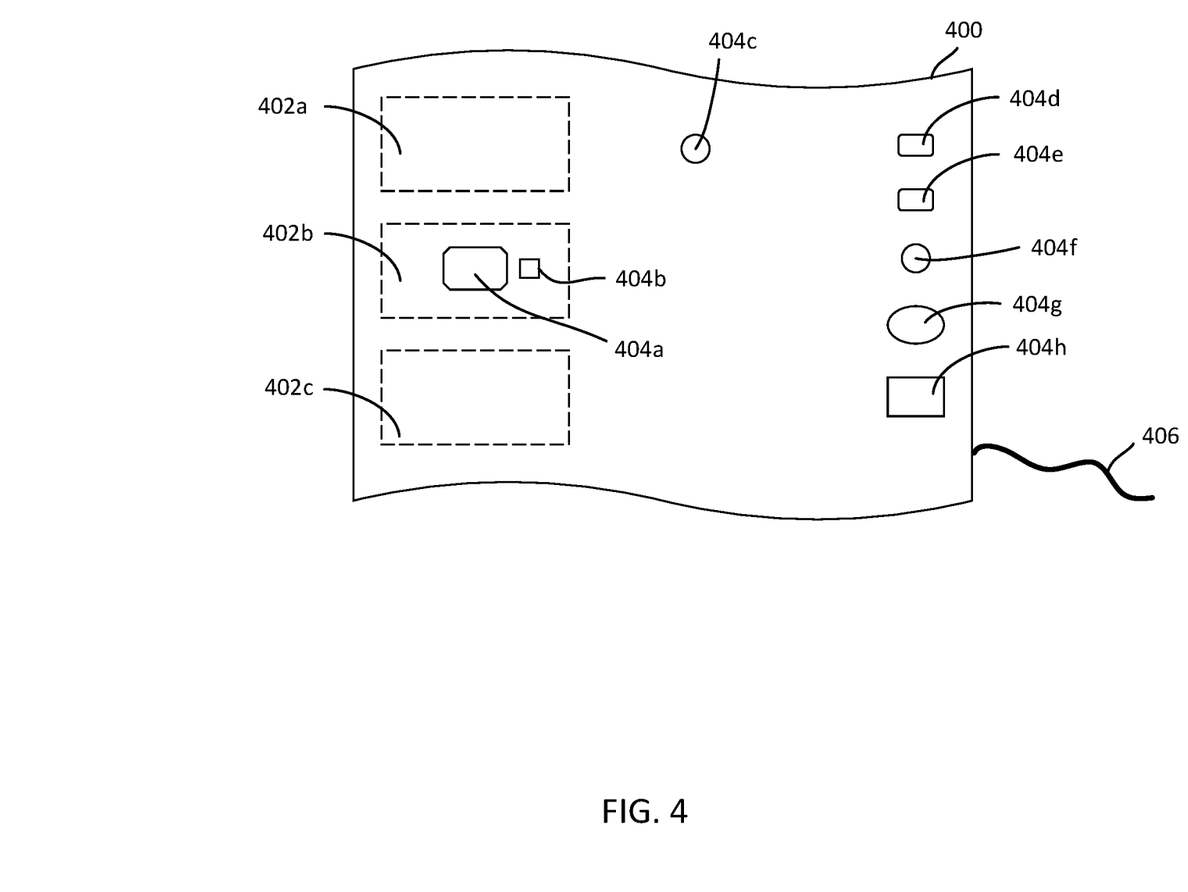
FIG. 4 is a schematic of a warming and monitoring blanket that can be worn by a patient during a dialysis treatment.

While the warming and monitoring articles described with respect to FIGS. 1-3B have been shown as gloves and socks, the warming and monitoring article may instead be a blanket or a wrap as shown in FIG. 4. The blanket in FIG. 4 includes heating elements 402a-c, sensors 404a-f, a transmitter 404g, a control device 404h, and an electrical cable 406. For example, during peritoneal dialysis, as the access to the patient is through the patient's abdomen, it may be advantageous for the patient to use a blanket or a wrap where sensors, such as an accelerometer 404b and a wetness sensor 404a, may be positioned proximate to the patient's access.

The warming and monitoring articles as described above are described as having a control device with a touch screen through which the patient or an operator can control the heating of the individual heating elements in the article. In some implementations, the heating of the individual heating elements may be performed with a device external to the article, e.g., a remote control device or the hemodialysis machine. The hemodialysis machine, for example, may include a graphical user interface for turning on/off heating elements. In some implementations, the control device may present treatment information (e.g., an elapsed time, a time remaining, a pumping rate) to the patient during treatment.

The warming and monitoring articles described above are described as being able to transmit information from sensors in the article to a dialysis machine via a transmitter in the article. In some implementations, the dialysis machine is configured to send information to the article to change the performance of the article or to display information on the control device. For example, based on a body temperature reading at a temperature sensor on the article, the controller of the dialysis machine may determine that more or less patient heating is necessary and may prompt a user to turn on or off certain heating elements.

The warming and monitoring articles described above are described as having wired connections from the sensors to the transmitter in the article. In some implementations, the sensors in the article may communicate wirelessly (e.g., via Bluetooth, Wi-Fi, NFC, etc.) with the transmitter in the article. In some implementations, the sensors in the article may communicate wirelessly directly to the hemodialysis machine.

A number of implementations have been described. Nevertheless, it will be understood that various modifications may be made. Accordingly, other implementations are within the scope of the claims.

What is claimed is:

1. An article configured to warm and monitor a patient during a dialysis treatment, the article comprising:
   one or more heating elements;
   one or more sensors configured to monitor a condition of the patient during the dialysis treatment;
   a fabric portion configured to receive the one or more heating elements and the one or more sensors and position the one or more heating elements and the one or more sensors on the patient during treatment;
   a transmitter configured to transmit information from the one or more sensors to a dialysis machine; and
   an electrical connector configured to provide power to at least one of the one or more heating elements and the one or more sensors,
   wherein the article is a glove or a sock.

2. The article of claim 1, wherein the one or more heating elements are individually controllable.

3. The article of claim 1, wherein the one or more sensors includes an ambient temperature sensor configured to monitor an ambient temperature of a space in which the dialysis treatment is occurring.

4. The article of claim 1, wherein the one or more sensors includes a blood oxygen monitor.

5. The article of claim 1, wherein the one or more sensors includes a blood pressure monitor.

6. The article of claim 1, wherein the one or more sensors includes a heart rate monitor.

7. The article of claim 1, wherein the one or more sensors includes a temperature sensor.

8. The article of claim 1, wherein the one or more sensors includes a wetness sensor.

9. The article of claim 8, wherein the wetness sensor is configured to be positioned proximate to a patient access and is configured to detect a leak at the patient access when the article is on the patient.

10. The article of claim 1, wherein the one or more sensors includes an accelerometer.

11. The article of claim 1, wherein the one or more heating elements are separable from the fabric portion of the article.

12. The article of claim 1, wherein the one or more sensors are separable from the fabric portion of the article.

13. The article of claim 1, wherein the article is configured to receive information from the dialysis machine, wherein the received information is based on, at least in part, the transmitted information.

14. The article of claim 13, wherein the article is configured such that performance of the article is changed based on the received information from the dialysis machine.

15. The article of claim 14, wherein the article is configured to display the received information from the dialysis machine.

16. The article of claim 1, wherein the article is a glove comprising a hand-covering portion and a forearm sleeve portion, the hand-covering portion comprising at least a portion of the one or more heating elements and the forearm sleeve portion comprising the one or more sensors and the transmitter.

17. The article of claim 16, wherein the one or more heating elements comprise a finger heating element and a palm heating element, both the finger heating element and the palm heating element being located on a first side of the article.

18. The article of claim 17, wherein the one or more heating elements comprise an additional finger heating element and a back-of-hand heating element, both the additional finger heating element and the back-of-hand heating element located on a second side of the article opposite the first side.

19. A dialysis system comprising:
a dialysis machine; and
an article configured to communicate with the dialysis machine during a dialysis treatment, the article comprising:
one or more heating elements;
one or more sensors configured to monitor a condition of the patient during the dialysis treatment;
a fabric portion configured to receive the one or more heating elements and the one or more sensors and position the one or more heating elements and the one or more sensors on the patient during treatment;
a transmitter configured to transmit information from the one or more sensors to the dialysis machine; and
an electrical connector configured to provide power to at least one of the one or more heating elements and the one or more sensors,
wherein the article is a glove or a sock.

20. The dialysis system of claim 19, wherein the electrical connector connects the article to the dialysis machine.

21. The dialysis system of claim 19, wherein the dialysis machine comprises a controller configured to determine a condition of a patient based on the information transmitted to the dialysis machine from the transmitter.

22. The dialysis system of claim 21, wherein the controller is further configured to raise an alarm on the dialysis machine based on a determined condition of the patient.

23. The dialysis system of claim 22, wherein the condition of the patient comprises information that the patient is disconnected from the dialysis machine.

24. The dialysis system of claim 21, wherein the dialysis machine comprises a pump configured to pump blood and the controller of the dialysis machine is configured to control a pump speed of the pump based on, at least in part, the transmitted information.

25. The dialysis system of claim 19, wherein the article is configured to receive information from the dialysis machine, wherein the received information is based on, at least in part, the transmitted information.

26. The dialysis system of claim 19, wherein the article is a glove comprising a hand-covering portion and a forearm sleeve portion, the hand-covering portion comprising at least a portion of the one or more heating elements and the forearm sleeve portion comprising the one or more sensors and the transmitter.

27. The dialysis system of claim 26, wherein the one or more heating elements comprise a finger heating element and a palm heating element, both the finger heating element and the palm heating element being located on a first side of the article.

28. The dialysis system of claim 27, wherein the one or more heating elements comprise an additional finger heating element and a back-of-hand heating element, both the additional finger heating element and the back-of-hand heating element located on a second side of the article opposite the first side.

* * * * *